(12) United States Patent
Arenson et al.

(10) Patent No.: US 7,175,855 B1
(45) Date of Patent: Feb. 13, 2007

(54) ZIPRASIDONE SUSPENSION

(75) Inventors: Daniel R. Arenson, East Lyme, CT (US); Hong Qi, Northbrook, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/573,312

(22) Filed: May 18, 2000

Related U.S. Application Data

(60) Provisional application No. 60/136,268, filed on May 27, 1999.

(51) Int. Cl.
*A61K 31/50* (2006.01)
*A61K 31/495* (2006.01)
*A61K 9/14* (2006.01)

(52) U.S. Cl. ..................... 424/489; 514/249
(58) Field of Classification Search ............... 514/249; 424/489
See application file for complete search history.

(56) References Cited

U.S. PATENT DOCUMENTS

| 4,831,031 | A |   | 5/1989  | Lowe, III et al. ............ 514/254 |
| 5,312,925 | A | * | 5/1994  | Allen et al. |
| 5,780,051 | A | * | 7/1998  | Eswara et al. |
| 5,795,909 | A | * | 8/1998  | Shashoua et al. |
| 5,906,991 | A |   | 5/1999  | Wachter et al. |
| 6,020,384 | A |   | 2/2000  | Wachter et al. |
| 6,150,366 | A |   | 11/2000 | Arenson et al. ............ 514/253 |

FOREIGN PATENT DOCUMENTS

| CA | 1218601      | 3/1987  |
| EP | 0 136 100    | 8/1984  |
| EP | 0 722 719 A1 | 7/1996  |
| EP | 0965343      | 8/1999  |
| WO | WO0072847    | 12/2000 |

OTHER PUBLICATIONS

Remington: The Science and Practice of Pharmacy, Nineteenth ed. vol. II, 1995, Chapter 80.*
Kuntz, Sifting through the ingredient Options, Food Product Design, Jun. 1995.*
Martin, Physical Pharmacy, 1993, p. 477-486.*
Pharmaceutical Dosage Forms and Drug Delivery Systems, by Ansel et al., 7$^{th}$ Ed. p. 90.
Handbook of Pharmaceutical Excipients, edited by Kibbe, 3$^{rd}$ Ed. p. 143.
Chinese version of Sprowls American Pharmacy, ed. By Dittert, pp. 196-212.
Alfonso R. Gennaro, Pharmacia Remington- Buenos Aires, Editorial Medica-Panamericana. 20th edition—2003 vol. 1 pp. 367-372, 864-866 and 1146.
Helman, Jose, Helman Pharmacotechnics. Mexico 2nd impresion, Editorial Continental S.A. 1982. pp. 501-509, 2070 and 2324.
J. Gerlach et al., "New antipschotics: the present status", International Clinical Psychopharmacology (1995), vol. 10 Suppl. 3, pp. 39-48.
Remington Pharmacy (pp. 367-373, 864-866, 1146, 1206, 1207, 12220).

\* cited by examiner

*Primary Examiner*—San-Ming Hui
(74) *Attorney, Agent, or Firm*—Steve T. Zelson; Kristina L. Konstas

(57) ABSTRACT

Compositions comprising ziprasidone free base or a difficult to wet pharmaceutically acceptable ziprasidone acid addition salt, a polysorbate, and colloidal silicon dioxide form good aqueous suspensions having a useful shelf life and are easily re-suspended if setting occurs.

5 Claims, No Drawings

ZIPRASIDONE SUSPENSION

This application is filed claiming priority from Provisional Application No. 60/136,268 filed May 27, 1999.

FIELD OF THE INVENTION

This invention relates to an oral suspension comprising ziprasidone free base or a pharmaceutically acceptable ziprasidone acid addition salt, a polysorbate, colloidal silicon dioxide, a viscosity agent, and water. In a more specific aspect, the invention relates to such a suspension which is taste masked. The invention further relates to a method of treating a psychosis with such a formulation.

BACKGROUND OF THE INVENTION

Ziprasidone is known compound having the structure:

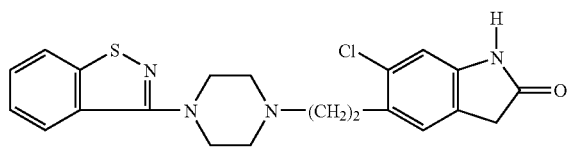

It is disclosed in U.S. Pat. Nos. 4,831,031 and 5,312,925, both of which are herein incorporated by reference in their entirety, has utility as a neuroleptic, and is thus useful, inter alia, as an antipsychotic. It is typically administered orally as the hydrochloride and addition salt, ziprasidone hydrochloride monohydrate. The hydrochloride salt is advantageous in that it is a high permeability drug, a factor which favorably affects bioavailability. The hydrochloride salt, as well as other ziprasidone acid addition salts, does, however, possess relatively poor aqueous solubility, a factor which unfavorably affects bioavailability.

Difficult to wet pharmaceutically acceptable compounds can be problematic in the pharmaceutical arts from a formulations perspective. For example, ziprasidone hydrochloride, in addition to having low solubility, is difficult to wet with an aqueous medium, and thereby presents special problems from the standpoint of trying to form an aqueous suspension. In the discussion which follows, ziprasidone hydrochloride is discussed as an exemplary member of the class composed of ziprasidone free base and ziprasidone acid addition salts which are difficult to wet. The invention is not to be taken as being limited to ziprasidone hydrochloride, however.

Owing to difficulties in wetting ziprasidone acid addition salts such as ziprasidone hydrochloride, the material is difficult to adequately suspend in an aqueous medium without having to resort to using long periods of high shear mixing. An ordinary laboratory homogenizer generally does not wet ziprasidone hydrochloride without being run for a very long time. Long blending periods almost inevitably lead to foaming and still yield poor results with drug aggregates still being visibly present, entrained in the foam. Thus, ziprasidone hydrochloride tends to float on the surface of water and other aqueous media and can be induced to form a suspension only with physical measures (high shear mixing for long times) that are considered extreme.

An alternative mixing procedure comprises first adding only a small amount of water to the ziprasidone salt, followed by grinding to wet the bulk drug substance. This wets the mass sufficiently so that it can be suspended in water. This procedure is still disadvantageous however in that it is difficult to scale up. Moreover, once ziprasidone hydrochloride has been induced to form an aqueous suspension in this fashion, an additional challenge is the prevention or retarding of rapid re-setting, which occurs relatively quickly with ziprasidone hydrochloride, generally within an hour or so, depending on the particle size. Settling can be particularly problematic for a pharmaceutical suspension since the suspension must be adequately re-suspended to ensure that an adequate dosage is administered to the patient.

One approach to improving the anti-setting properties of a suspension is to use a viscosity agent such as any of the natural gums or cellulosics, such as hydroxypropylcellulose (HPC) or hydroxypropylmethylcellulose (HPMC) to increase viscosity, and thereby retard the rate of re-setting of wetted particles in the suspension. Such an approach has been found to be problematic in the case of ziprasidone hydrochloride since, once a viscosity agent has been added, when the ziprasidone hydrochloride eventually settles, it tends to form a thin cake which sits on the bottom and can be very difficult to break up and to re-suspend. Such caking is facilitated by temperature fluctuations and by vibrations such as those which occur during normal handling and transportation.

Further, in the specific case of ziprasidone acid addition salts, such salts generally exhibit a very bitter taste, the degree of bitterness increasing with increasing solubility of the particular salt. Sugars, with or without the presence of other sweetening and/or flavoring agents, are generally insufficient to mask the bitter taste. Adjusting the pH to form the less soluble, hence less bitter, free base, is an option for decreasing bitterness. However, such adjustment can lead to changes in particle size if very careful and continuous control is not maintained. Substantial changes in particle size can, in turn, undesirably lead to changes in bioavailability.

Thus, a suspension comprising ziprasidone free base or ziprasidone hydrochloride (or other pharmaceutically acceptable ziprasidone addition salt) which maintains an improved shelf life (i.e., which maintains a longer period of suspension prior to re-settling) and which is easily re-suspendible would represent a valuable addition to the formulations arts. In the particular case of a suspension of a ziprasidone acid addition salt, a suspension with improved taste would be a further valuable addition.

SUMMARY OF THE INVENTION

It has now been determined that dry components comprising ziprasidone free base or a difficult to wet pharmaceutically acceptable ziprasidone acid addition salt, a polysorbate, a viscosity agent, and colloidal silica easily form a good suspension in aqueous media. Thus one aspect of the invention is a composition of matter which is a suspension comprising ziprasidone free base or a difficult to wet pharmaceutically acceptable ziprasidone acid addition salt, water, a polysorbate, a viscosity agent, and colloidal silicon dioxide. By "difficult to wet" it is meant a pharmaceutically acceptable salt of ziprasidone that does not readily form a suspension in water when mixed by ordinary means such as a laboratory blender which has been run at normal speed for ten minutes. Such salts do not, by themselves, form a "good suspension", as defined below, in water.

Again, it is noted ziprasidone hydrochloride is used herein to exemplify the invention, although it is to be understood that the use of an example is not to be considered as limiting.

The particle size of the ziprasidone hydrochloride particles is not considered particularly important in terms of ability to be wetted, although the mean particle size is generally below or equal to 85 µm.

Pre-constituted suspensions according to the invention exhibit good suspension and can be remixed upon settling. By "good suspension" it is meant (1) that in a suspension according to the invention there is no visible settling for greater than 24 hours at room temperature (RT, usually 25° C.), preferably for greater than one week and (2) that when visible settling does occur, resuspension is easily effected by simple physical mixing such as gentle manual stirring or moderate manual shaking, high shear mixing not being required.

The invention is surprising in that polysorbates are the only wetting agents among a range of wetting agents that were tested which yielded positive results. Other wetting agents such as sodium lauryl sulfate caused foaming before adequate wetting could be obtained. Such foaming was problematic in that, although some particles appeared to wet, other salt particles became entrained in the foam, and still other salt particles sat as a dry mass atop the water, with the result that a homogeneous suspension did not form. Thus, polysorbates are useful as agents in the instant invention that allowed complete wetting below the level at which they foam.

The term "polysorbate" is employed for its art-recognized meaning, i.e., polyoxyethylene sorbitan fatty acid esters as disclosed and defined in the *Handbook Of Pharmaceutical Excipients,* edited by Ainley Wade and Paul Weller, The Pharmaceutical Press, London, 1994. Useful polysorbates include polysorbate 20, 21, 40, 60, 61, 65, 80, 81, 85, and 120. Polysorbate 80 is preferred.

The colloidal silicon dioxide useful herein is of the type known in the art (e.g., of the type available commercially as CAB-O-SIL®, registered trademark of Cabot Corporation, Boston, Mass.) and, while not wishing to be bound by any particular theory or mechanism, is believed to function as an anti-caking agent. That is, even though some re-settling may occur in a suspension according to the invention, the re-settled material does not cake, meaning that, even though a viscosity agent is present, resettled material does not form a firm mass that is difficult to break up and re-disperse in the presence of colloidal silicon dioxide. In the presence of colloidal silicon dioxide, anti-caking properties are effected such that re-suspension can be effected in simple physical mixing, as previously described. Thus the advantages of the invention is that the combination of a polysorbate and colloidal silicon dioxide achieves good wetting together with facile re-suspendability in the event settling occurs.

In a more specific aspect of the invention, there is provided an aqueous suspension of ziprasidone comprising a ziprasidone acid addition salt suspended in an aqueous pharmaceutically acceptable carrier which contains an alkali metal (e.g., sodium, lithium, or potassium) chloride or an alkaline earth metal (e.g. magnesium or calcium) chloride. It has been determined that these salts are very effective as taste masking agents. While not wishing to be bound by theory or statements of mechanism, it is believed that such salts reduce the solubility, and thereby the dissolved amount and/or concentration, of ziprasidone salt in the suspension. Reduced concentration of dissolved ziprasidone is not a disadvantage in a suspension dosage form, however, and in the instant invention is advantageous since suspended ziprasidone is more chemically stable than dissolved ziprasidone, thereby improving chemical stability, as well as taste.

The invention further provides a method of treating a psychosis, comprising administering to a patient in need of such treatment an effective amount of a suspension comprising ziprasidone free base or a pharmaceutically acceptable ziprasidone acid addition salt, a polysorbate, a viscosity agent, colloidal silicon dioxide, and water, said suspension being otherwise disclosed an described herein.

Ziprasidone hydrochloride can be used in any active crystalline or amorphous form, although crystalline ziprasidone hydrochloride monohydrate is preferred.

DETAILED DESCRIPTION

In general, the polysorbate is used in an amount which is at least sufficient to effect complete wetting, i.e., meaning that drug is easily dispersed within a reasonable amount of time. The amount of polysorbate employed should not, as an upper limit, equal or exceed the amount which causes foaming.

Colloidal silicon dioxide is used in at least an anti-caking amount, i.e., an amount such that a firm, difficult to re-suspend cake does not form under normal conditions of transportation and storage. It is possible that re-settling may occur which is easily re-suspended by mild physical agitation (e.g., stirring or shaking). The upper limit for colloidal silicon dioxide is an amount above which, in conjunction with the viscosity agent, causes gelation. The particular grade of colloidal silicon dioxide, so long as it is pharmaceutically acceptable, has not been found to be critical.

Both the amount of polysorbate and colloidal silicon dioxide are system specific, optimum amounts depending on the drug form (e.g., free base versus acid salt), and the amounts and types of other excipients which may also be used as part of the suspension. Generally, the polysorbate will be employed in an amount of from about 0.01 to about 2.0 by weight % based on the weight of the final suspension, more preferably from about 0.05 to about 0.30 weight %. The colloidal silicon dioxide will generally be employed in an amount of from 0.05 weight % to 2.0 weight % based on the weight of the suspension.

A suitable viscosity agent (also referred to in the art as a "thickening agent") is also used as a component of the invention. Such viscosity agents function as suspending agents and include, for example, hydrocolloid gums known for such purpose, examples of which include xanthan gum, guar gum, locust bean gum, gum tragacanth, and the like. Alternatively, synthetic suspending agents may be used such as sodium carboxymethylcellulose, polyvinylpyrrolidone, hydroxypropylcellulose hydroxypropylmethylcellulose, and the like. The viscosity agent is generally used in an amount of from about 0.01 weight % to about 10 weight % based on the weight of the suspension. The amount actually used in a particular formulation is dependent on the exact agent and on other excipients present.

Ziprasidone free base or an acid addition salt can be used in this invention in any form, including anhydrous or hydrated. The ziprasidone hydrochloride employed herein, including the examples, was ziprasidone hydrochloride monohydrate, and is generally referred to throughout simply as ziprasidone hydrochloride for convenience. The invention is applicable to other ziprasidone acid addition salts as well, such as acetic acid, lactic, succinic, maleic, tartaric, citric, gluconic, ascorbic, benzoic, cinnamic, fumaric, sulfuric, phosphoric, hydrobromic, hydroiodic, sulfamic, sulfonic such as methanesulfonic, benzenesulfonic, and related acids.

As previously stated, it is advantageous to include a taste masking agent in the suspension in the specific case of pharmaceutically acceptable ziprasidone acid addition salts. Such taste masking agents are alkali metal and alkaline earth metal chlorides including sodium chloride, lithium chloride, potassium chloride, magnesium chloride, and calcium chloride. Sodium chloride is preferred. The taste masking agent is generally included in the suspension in a taste-masking amount, generally an amount of about 0.5 to about 2.0 weight % as sodium chloride based on the weight of the suspension. For other salts, equivalent molar amounts can be calculated.

A composition according to the invention is an oral, pre-constituted suspension which contains, as necessary ingredients, ziprasidone free base or a ziprasidone acid addition salt, water, a polysorbate, a viscosity agent, and colloidal silicon dioxide. Compositions according to the invention can also contain other conventional pharmaceutically acceptable excipients such as, for example: flavorings, buffers, pH adjusting agents, diluents, colors, preservatives, and sweetening agents. Some excipients can serve multiple functions.

Flavors incorporated in the composition may be chosen from synthetic flavor oils and flavoring aromatics and/or natural oils, extracts from plant leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essence, including apple, banana, pear, peach, strawberry, raspberry, cherry, plum, pineapple, apricot, and so forth. The amount of flavoring may depend on a number of factors including the organoleptic effect desired. Generally the flavoring will be present in an amount of from about 0.01 to about 1.0 percent by weight based on the total suspension weight, when a flavor is used.

The suspension can be manufactured by conventional pharmaceutical methods, combining the various components using conventional equipment such as an overhead stirrer, usually at about 100–500 RPM. Many different orders of adding components to the stirrer can be employed. A typical order of mixing in the instant invention, although others are certainly possible, is (1) adding the water heated to 70° C. for any components which require temperatures higher than room temperature (rt) as an aid to dissolution (if no such ingredients are employed, then heating is not required); (2) cooling to rt (about 30°C.); then adding, in the following order (and assuming each component is employed), viscosity agent, sweetener, buffer, polysorbate, taste masking agent if employed, ziprasidone, colloidal silicon dioxide, and flavors.

The invention is further exemplified and disclosed by the following non-limiting examples:

EXAMPLE 1

A suspension formulation was prepared by heating 733.31 g of water to 70° C. followed by adding 1.36 g methylparaben and 0.17 g propylparaben while stirring at about 200 rpm with an overhead stirrer. After the parabens completely dissolved, the temperature was lowered to about 30° C. The following components were then added in order: 2.78 g xanthan gum, 333.90 g xylitol, 1.13 g anhydrous citric acid, 1.21 g trisodium citrate dihydrate, 0.55 g polysorbate 80, 11.13 g NaCl, 11.33 g ziprasidone hydrochloride monohydrate having a nominal particle size of 38 μm, 11.13 g colloidal silicon dioxide, and 5.0 g cherry flavor. The pH was adjusted to 4.0 using aqueous sodium hydroxide and hydrochloric acid as needed.

EXAMPLE 2

This example discloses a process for making a ziprasidone free base suspension.

Into a 2 liter beaker was weighted 812.0 g of water which was stirred using an overhead stirrer at a speed of about 200 rpm. The water was heated to 70° C. Once the temperature reached 70° C., 1.36 g of methylparaben and 0.17 g of propylparaben were added. When the parabens were completely dissolved, the temperature was lowered to 40° C. To the solution was slowly added 3.27 g of a viscosity agent, CARBOPOL® resin 974P (Union Carbide Corporation, Danbury, Conn.), taking care to avoid big lumps, and increasing the stirring speed as necessary. Agitation was maintained until the viscosity agent had completely dispersed and/or dissolved. To the solution was added 218 g of sucrose. After dissolving the sucrose, temperature was lowered to 30° C. To the solution was added 2.94 g of trisodium citric salt. To the solution was added 0.544 g of polysorbate 80. To the solution was slowly added 11.325 g of ziprasidone free base. A 10% NaOH solution was used to adjust the pH of the formulation to 5.7. After the pH had equilibrated, 1.09 g of colloidal silicon dioxide (CAB-O-SIL®, Cabot Corporation) was added.

EXAMPLE 3

This example illustrates the results obtained using colloidal silicon dioxide as an anti-caking agent as compared to other agents used for the same purpose.

Ziprasidone free base suspensions (nominal ziprasidone particle size of 38 μm) containing the same components, except for the anti-caking agent, where made as in Example 2, with and without each of the anti-caking agents listed below. Each anti-caking agent was added into the formulation in a 60 cc bottle, which was then centrifuged at 2000 RPM for 20 minutes to accelerate settling, and the bottles were then gently rotated at a speed of about one rotation every 2 seconds to resuspend the settled solids. The time required for the formulations to become fully homogeneous (no solids stuck at the bottom of the bottle by visual inspection) was recorded. The data support that the time required for the formulations to resuspend is substantially reduced using colloidal silicon dioxide (CSD in the Table below), reducing resuspension time substantially at about 0.3% level.

| No. | Anti-caking Agent | Level (w/w %) in Formulation | Resuspendability |
| --- | --- | --- | --- |
| 1 | None | | >20 minutes |
| 2 | MCC*, 200 μm** | 3.0 | >20 minutes |
| 3 | MCC, 50 μm | 1.0 | >20 minutes |
| 4 | SiO$_2$ | 1.0 | ~2 minutes |
| 5 | CSD | 0.3 | ~1 minutes |
| 6 | Magnesium Stearate | 0.2 | >20 minutes |

*MCC is an acronym for microcrystalline cellulose
**Particle sizes, given in microns, are nominal

EXAMPLE 4

Different surfactants were tested for their ability to wet ziprasidone HCl monohydrate in water: sodium lauryl sulfate (SLS), MIGLYOL® (registered trademark of Dynamit Nobel Aktiengesellschaft, Germany) Triglyceride (810), and polysorbate-80. In three separate 100 mL volumes of water, each surfactant listed above was added in an amount to make a 1% solution. MIGLYOL® was added in excess due to its low solubility. While stirring at 200 rpm with an overhead stirrer, to each of the three surfactant solutions was added 1.132 g of ziprasidone was added to each of the three surfactant solutions (equivalent to 10 mgA/ml). The observed rate of wetting was recorded as follows:

| | |
|---|---|
| 1) SLS | >20 min |
| 2) MIGLYOL ® triglyceride | >20 min |
| 3) Polysorbate-80 | <2 min |

Only the polysorbate 80 solution did not show any visible aggregates after mixing overnight.

Further testing of polysorbate-80 at different concentrations demonstrated that a concentration as low as 0.05% can significantly decrease drug wetting time.

| Conc. (%) | Drug wetting time |
|---|---|
| 0.05 | 4 min |
| 0.15 | 3.8 min |
| 0.25 | 3.5 min |

What is claimed is:

1. A composition comprising ziprasidone hydrochloride, water, from about 0.05 to about 0.3 weight % of a polysorbate 80, from about 0.01 to about 10 weight % of xanthan gum, and from about 0.05 to about 2.0 weight % of colloidal silicon dioxide.

2. The composition as defined in claim 1 further comprising from about 0.5 to about 2.0 weight % of a taste masking agent selected from the group consisting of an alkali metal chloride and an alkaline earth metal chloride.

3. The composition as defined in claim 2, wherein said alkali metal chloride is selected from the group consisting of sodium chloride, potassium chloride, and lithium chloride.

4. The composition as defined in claim 3, wherein said alkali metal chloride is sodium chloride.

5. The composition as defined in claim 2, wherein said alkaline earth metal chloride is magnesium chloride or calcium chloride.

* * * * *